United States Patent [19]

Diehr

[11] Patent Number: 5,708,184
[45] Date of Patent: Jan. 13, 1998

[54] PROCESS FOR THE PREPARATION OF SUBSTITUTED AMINOCARBONYLTRIAZOLINONES

[75] Inventor: Hans-Joachim Diehr, Wuppertal, Germany

[73] Assignee: Bayer Aktiengesellschaft, Leverkusen, Germany

[21] Appl. No.: 686,079

[22] Filed: Jul. 24, 1996

[30] Foreign Application Priority Data

Jul. 31, 1995 [DE] Germany .................... 195 28 055.5

[51] Int. Cl.$^6$ ............................................. C07D 249/12
[52] U.S. Cl. ............................................. 548/263.8
[58] Field of Search ............................................. 548/263.8

[56] References Cited

U.S. PATENT DOCUMENTS

| | | | |
|---|---|---|---|
| 5,021,080 | 6/1991 | Muller et al. | 548/263.8 |
| 5,194,085 | 3/1993 | Lindig et al. | 504/273 |
| 5,273,958 | 12/1993 | Kuhnt et al. | 548/263.8 |
| 5,326,877 | 7/1994 | Lindig et al. | 548/263.8 |
| 5,461,149 | 10/1995 | Lindig et al. | 548/263.8 |

FOREIGN PATENT DOCUMENTS

| | | |
|---|---|---|
| 294666 | 12/1988 | European Pat. Off. . |
| 370293 | 5/1990 | European Pat. Off. . |

OTHER PUBLICATIONS

Cram & Hammond, "Organic Chemistry", 2nd Ed. pp. 565–567 (1964).

Chemical Abstracts, vol. 122, P. 1079, Abstract No. 9682u, Abstract of JP 06-228,080 (1995).

Primary Examiner—Patricia L. Morris
Attorney, Agent, or Firm—Sprung Kramer Schaefer & Briscoe

[57] ABSTRACT

The invention relates to a new process for the preparation of substituted amino-carbonyltriazolinones of the general formula (I)

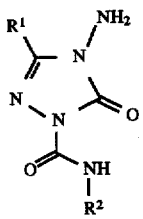

in which $R^1$ and $R^2$ have the meanings given in the description.

11 Claims, No Drawings

PROCESS FOR THE PREPARATION OF SUBSTITUTED AMINOCARBONYLTRIAZOLINONES

The invention relates to a new processes for the preparation of substituted amino-carbonyltriazolinones which are known as herbicidally active compounds.

It is known that certain substituted aminocarbonyltriazolinones, such as, for example, the compound 4-amino-5-methyl-2-t-butylaminocarbonyl-2,4-dihydro-3H-1,2,4-triazol-3-one, are obtained when corresponding triazolinones, such as, for example, the compound 4-amino-5-methyl-2,4-dihydro-3H-1,2,4-triazol-3-one, are reacted with isocyanates, such as, for example, t-butyl isocyanate, in the presence of a reaction auxiliary, such as, for example, diazabicycloundecene (DBU), and in the presence of a diluent, such as, for example, acetonitrile (cf. EP 294666, cf. also EP 370293).

In this procedure, however, the substituted aminocarbonyltriazolinones desired are contaminated substantially by products of two additions of isocyanate and are thus also obtained in unsatisfactory yields.

To prepare substituted aminocarbonyltriazolinones in satisfactory quality it was therefore previously necessary to use a protective group for the amino group and then to eliminate the protective group after the reaction with an isocyanate. This three-step reaction sequence results in yield losses, in particular also bemuse even the substituted aminocarbonyltriazolinones are not entirely stable under the acidic conditions required for eliminating the protective group.

It has now been found that substituted aminocarbonyltriazolinones of the general formula (I)

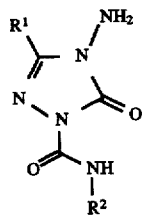

in which
$R^1$ represents a radical from the series consisting of alkyl, alkoxy, alkylthio, alkylamino and dialkylamino, each of which is optionally substituted,
$R^2$ represents a radical from the series consisting of alkyl, alkenyl, alkinyl, cycloalkyl, cycloalkylalkyl, arylalkyl, arylalkenyl or arylalkinyl, each of which is optionally substituted,
are obtained in very good yields and in high purity
when substituted triazolinones of the general formula (II)

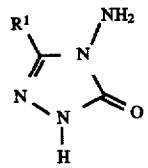

in which
$R^1$ has the abovementioned meaning
are reacted with isocyanates of the general formula (III)

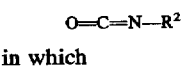

in which $R^5$ has the abovementioned meaning at temperatures between 0° C. and 150° C., in the presence of a reaction auxiliary, in the presence of a basic compound and in the presence of a diluent.

Surprisingly, the substituted aminocarbonyltriazolinones of the general formula (I) can be prepared by the process according to the invention in considerably higher yields and in substantially better quality than by the prior art.

The process according to the invention thus represents a valuable enrichment of the prior art.

The process according to the invention preferably relates to the preparation of compounds of the formula (I) in which $R^1$ represents a radical from the series consisting of alkyl, alkoxy, alkylthio, alkylamino or dialkylamino, each of which has 1 to 6 carbon atoms and each of which is optionally substituted by cyano, halogen or $C_1$–$C_4$-alkoxy, $R^2$ represents a radical from the series consisting of alkyl, alkenyl, alkinyl, each of which has 1 to 12 carbon atoms and each of which is optionally substituted by cyano or halogen, or represents a radical from the series consisting of $C_3$–$C_6$-cycloalkyl, $C_3$–$C_6$-cycloalkyl-$C_1$–$C_4$-alkyl, phenyl-$C_1$–$C_4$-alkyl, phenyl-$C_2$–$C_4$-alkenyl or phenyl-$C_2$–$C_4$-alkinyl, each of which is optionally substituted by cyano, halogen, $C_1$–$C_4$-alkyl, $C_1$–$C_4$-halogenoalkyl, $C_1$–$C_4$-alkoxy or $C_1$–$C_4$-halogenoalkoxy.

In particular, the process according to the invention relates to the preparation of compounds of the formula (I) in which $R^1$ represents methyl, ethyl, n- or i-propyl, n-, i-, s- or t-butyl, n-, i-, s- or t-pentyl, methoxy, ethoxy, n- or i-propoxy, m, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino or dipropylamino, each of which is optionally substituted by cyano, fluorine, chlorine, bromine, methoxy or ethoxy, $R^2$ represents methyl, ethyl, n- or i-propyl, n-, i-, s- or t-butyl, n-, i-, s- or t-pentyl, n-, i- or s-hexyl, propenyl, butenyl, pentenyl, propinyl, butinyl or pentinyl, each of which is optionally substituted by cyano, fluorine, chlorine or bromine, or represents cyclohexyl, cyclohexylmethyl, cyclohexylethyl, cyclohexylpropyl, benzyl, phenylethyl, phenylpropyl, phenylethenyl, phenylpropenyl, phenylethinyl or phenylpropinyl, each of which is optionally substituted by cyano, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, fluoroethoxy, difluoroethoxy or trifluoroethoxy.

If, for example, 4-amino-5-methyl-2,4-dihydro-3H-1,2,4-triazol-3-one and t-butylisocyanate are used as starting substances, the course of the reaction of the process according to the invention can be outlined by the following equation:

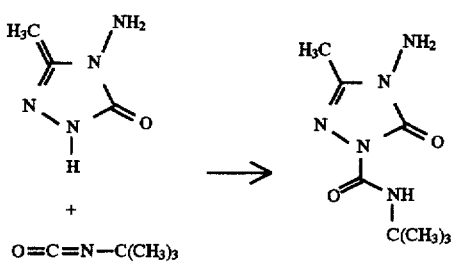

O=C=N—C(CH₃)₃

Formula (II) provides a general definition of the substituted triazolinones to be used as starting substances in the process according to the invention for the preparation of the compounds of the formula (I). In formula (II), $R^1$ preferably, or in particular, has the meaning which has already been mentioned above in the description of the compounds of the formula (I) to be prepared according to the invention as being preferred, or particularly preferred, for $R^1$.

The starting substances of the formula (II) are known and/or can be prepared by known processes (cf. EP 294666, EP 370293).

Formula (III) provides a general definition of the isocyanates furthermore to be used as starting substances in the process according to the invention. In formula (III), $R^2$ preferably, or in particular, has the meaning which has already been mentioned above in the description of the compounds of the formula (I) to be prepared according to the invention as being preferred, or particularly preferred, for $R^2$.

The starting substances of the formula (III) are known chemicals for synthesis.

The process according to the invention is carried out in the presence of a reaction auxiliary. Suitable reaction auxiliaries are preferably metal compounds which contain metals of relatively small volume. These include, in particular, compounds of lithium, sodium, magnesium and aluminum, especially the corresponding hydrides, hydroxides, acetates, carbonates, sulphates and halides. Reactants for the process according to the invention which may be particularly emphasized are lithium hydride, lithium hydroxide, lithium fluoride, lithium chloride and lithium bromide.

The process according to the invention is carried out in the presence of a basic compound. The basic compounds which are suitable in this context are, generally, the customary inorganic or organic bases or acid acceptors. These preferably include the acetates, amides, carbonates, hydrogen carbonates, hydrides, hydroxides or alkanolates of alkali metals or alkaline earth metals, such as, for example, sodium acetate, potassium acetate or calcium acetate, lithium amide, sodium amide, potassium amide or calcium amide, sodium carbonate, potassium carbonate or calcium carbonate, sodium hydrogen carbonate, potassium hydrogen carbonate or calcium hydrogen carbonate, lithium hydride, sodium hydride, potassium hydride or calcium hydride, lithium hydroxide, sodium hydroxide, potassium hydroxide or calcium hydroxide, sodium methanolate, sodium ethanolate, sodium n- or i-propanolate, sodium n-, i-, s- or t- butanolate, potassium methanolate, potassium ethanolate, potassium n- or i-propanolate or potassium n-, i-, s- or t-butanolate; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methylpiperidine, 1,4-diazabicyclo[2,2,2]-octane (DABCO), 1,5-diazabicyclo[4,3,0]-non-5-en (DBN), and 1,8 diazabicyclo[5,4,0]-undec-7-ene (DBU).

Basic compounds which are particularly preferably employed when carrying out the process according to the invention are sodium hydroxide, potassium hydroxide, 1,5-diazabicyclo[4,3,0]-non-5-ene (DBN) and 1,8 diazabicyclo [5,4,0]-undec-7-ene (DSU).

The process according to the invention is carded out in the presence of a diluent. Diluents which are preferably suitable are aprotic polar organic solvents. These preferably include dialkyl ethers, such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether, ethylene glycol diethyl ether, diethylene glycol dimethyl ether or diethylene glycol diethyl ether;, dialkyl ketones, such as, for example, acetone, butanone (methyl ethyl ketone), methyl i-propyl ketone or methyl i-butyl ketone, nitriles, such as, for example, acetonitrile, propionitrile, butyronitrile or benzonitrile; amides, such as, for example, N,N-dimethylformamide (DMF), N,N-dimethylacetamide, N-methylformanilide, N-methylpyrrolidone or hexamethylphosphoric triamide; esters, such as, for example, methyl acetate, ethyl acetate, n- or i-propyl acetate or n-, i- or s-butyl acetate; and also sulphoxides, such as, for example, dimethyl sulphoxide.

Diluents which are particularly preferably employed in the process according to the invention are methyl t-butyl ether, methyl t-pentyl ether, tetrahydrofuran, methyl acetate, ethyl acetate and acetonitrile.

When carrying out the process according to the invention, the reaction temperatures can be varied within a substantial range. In general, the process is carried out at temperatures between 0° C. and 150° C., preferably between 20° C. and 110° C., in particular between 40° C. and 80° C.

The process according to the invention is generally carried out under atmospheric pressure. However, it is also possible to carry out the process according to the invention under elevated or reduced pressure—in general between 0.1 bar and 10 bar.

To carry out the process according to the invention, between 0.9 and 1.5 mol, preferably between 1.0 and 1.4 mol, in particular between 1.1 and 1.3 mol, of isocyanate of the formula (III), between 0.001 and 1 mol, preferably between 0.01 and 0.1 mol, of reaction auxiliary and between 0.001 and 1 mol, preferably between 0.01 and 0.1 mol, of basic compound are generally employed per mole of substituted triazolinone of the formula (II).

In a preferred embodiment of the process according to the invention, a substituted triazolinone of the formula (II) together with a reaction auxiliary and a basic compound are introduced into a suitable diluent, and an isocyanate of the formula (III) is slowly metered into this mixture. The reaction mixture is then stirred until the reaction is virtually complete.

Working-up and isolation of the product of the formula (I) can be carried out by customary methods. For example, the mixture is filtered, and the solvent is carefully removed from the filtrate by distillation under reduced pressure, the desired product generally remaining in good quality in the form of a residue. If desired, it can be purified further in the customary manner, for example by recrystallization.

The substituted aminocarbonyltriazolinones of the general formula (I) to be prepared by the process according to the invention have already been disclosed as herbicidally active compounds (cf. EP 294666, EP 370293).

PREPARATION EXAMPLES

EXAMPLE 1

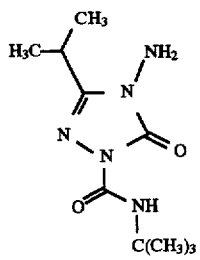

Within approximately 20 minutes, 54.5 g (0.55 mol) of t-butyl isocyanate are added dropwise with stirring to a mixture, heated to 55° C. to 60° C., of 72.8 g (0.50 mol) of 4-amino-5-i-propyl-2,4-dihydro-3H-1,2,4-triazol-3-one (purity 97.6%), 0.8 g of potassium hydroxide flakes (purity 88%), 0.5 g of lithium chloride and 500 ml of methyl acetate, and the reaction mixture is then refluxed for 3 hours. After the mixture has cooled to approximately 20° C., it is filtered, the solvent is carefully removed from the filtrate by distillation under a water pump vacuum, and the residue which remains is dried under a water pump vacuum at approximately 60° C.

122 g (content: 93.2%, i.e. yield: 94% of theory) of 4-amino-5-i-propyl-2-t-butyl-aminocarbonyl-2,4-dihydro-3H-1,2,4-triazol-3-one of a melting range of 158° C. to 162° C. are obtained.

EXAMPLE 2

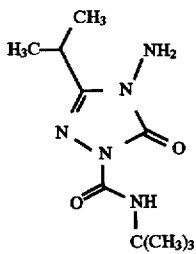

In the come of approximately 12 minutes, 21.8 g (0.22 moo of t-butyl isocyanate are added dropwise with stirring to a mixture, heated to 55° C. to 60° C., of 30.2 g (0.20 mol) of 4-amino-5-i-propyl-2,4-dihydro-3H- 1,2,4-triazol-3-one (purity 94.2%), 0.32 g of potassium hydroxide flakes (purity 88%), 0.20 g of lithium chloride and 200 ml of methyl acetate, and the reaction mixture is then refluxed for 3 hours. After the mixture has been cooled to approximately 20° C., the solvent is carefully removed from the filtrate by distillation under a water pump vacuum, and the residue which remains is dried under a water pump vacuum at approximately 60° C.

51.8 g (content: 93.9%, i.e. yield: 96% of theory) of 4-amino-5-i-propyl-2-t-butyl-aminocarbonyl-2,4-dihydro-3H-1,2,4-triazol-3-one of a melting range of 158° C. to 162° C. are obtained.

When carrying out the reaction analogously to Example 2, but without the use of lithium chloride, the compound 4-amino- 5-i-propyl-2-t-butylaminocarbonyl-2,4-dihydro-3H-1,2,4-triazol-3-one is only obtained in a yield of 73% of theory.

Other compounds of the formula (I) which can be prepared analogously to Examples 1 and 2 and following the general description of the process according to the invention are, for example, those listed in Table 1 below.

TABLE 1

Examples of the compounds to be prepared according to the invention

| Ex. No. | $R^1$ | $R^2$ | Melting point (°C.) | Yield (% of th.) |
|---|---|---|---|---|
| 3 | $C_3H_7$-i | $C_4H_9$-s | 68 | 100 |
| 4 | $C_3H_7$-i | $C_3H_7$-i | 132 | 100 |
| 5 | $C_3H_7$-i | $C_4H_9$-i | 84 | |
| 6 | $C_3H_7$-i | $CH_3$ | 174 | 98 |

Analogously to the process according to the invention, triazolinones of the formula (if) can be reacted equally successfully with diisocyanates, such as, for example, with hexamethylene diisocyanate, to give the corresponding 2:1 adducts.

It will be understood-that the specification and examples are illustrative but not limitative of the present invention and that other embodiments within the spirit and scope of the invention will suggest themselves to those skilled in the art.

I claim:

1. A process for the preparation of an aminocarbonyltriazolinone of the formula

wherein $R^1$ represents $C_1$–$C_6$-alkyl, $C_1$–$C_6$-alkoxy, $C_1$–$C_6$-alkylthio, $C_1$–$C_6$-alkylamino or $C_1$–$C_6$-dialkylamino, wherein each of which is optionally substituted by cyano, halogen or $C_1$–$C_4$-alkoxy, $R^2$ represents $C_1$–$C_{12}$-alkyl, $C_2$–$C_{12}$-alkenyl, or $C_2$–$C_{12}$-alkynyl, wherein said alkyl, alkenyl, or alkynyl groups are optionally substituted by cyano or halogen, or optionally substituted $C_3$–$C_6$-cycloalkyl, optionally substituted $C_3$–$C_6$-cycloalkyl-$C_1$–$C_4$-alkyl, optionally substituted phenyl-$C_1$–$C_4$-alkyl, or optionally substituted phenyl-$C_2$–$C_4$-alkynyl wherein said optional substituent is selected from the group consisting of cyano, halogen, $C_1$–$C_4$-alkyl, $C_1$–$C_4$-halogenoalkyl, $C_1$–$C_4$-alkoxy or $C_1C_4$-halogenalkoxy, which consists essentially of reacting a triazolinone of the formula

with an isocyanate of the formula

in the presence of a reaction auxiliary, a basic compound and optionally a diluent, wherein said reaction auxiliary is metal compound selected from the corresponding hydride, hydroxide, acetate, carbonate, sulphate and halide of lithium, sodium, magnesium and aluminum and wherein said basic compound is an inorganic or organic base.

2. The process according to claim 1, wherein $R^1$ represents methyl, ethyl, n- or i-propyl, n-, i-, s- of t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino or dipropylamino, each of which is optionally substituted by cyano, fluorine, chlorine, bromine, methoxy or ethoxy, $R^2$ represents methyl, ethyl, n- or i-propyl, n-, i-, s- or t-butyl, n-, i-, s- or t-pentyl, n-, i- or s-hexyl, propenyl, butenyl, pentenyl, propinyl, butinyl or pentinyl, each of which is optionally substituted by cyano, fluorine, chlorine or bromine, or represents cyclohexyl, cyclohexylmethyl, cyclohexylethyl, cyclohexylpropyl, benzyl; phenylethyl, phenylpropyl, phenylethenyl, phenylpropenyl, phenylethinyl or phenylpropinyl, each of which is optionally substituted by cyano, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, fluoroethoxy, difluoroethoxy or trifluoroethoxy.

3. The process according to claim 1, wherein the reaction is carried out in the presence of a diluent.

4. The process according to claim 1, wherein the reaction temperature is between 0° and 150° C.

5. The process according to claim 1, wherein the reaction is carried out under atmospheric pressure.

6. The process according to claim 1, wherein between 0.9 to 1.5 mol of isocyanate, between 0.001 and 1 mol of the reaction auxiliary and between 0.001 and 1 mol of the basic compound is used per mol of the triazolinone of formula II.

7. The process according to claim 1, wherein the reaction auxiliary is lithium hydride, lithium hydroxide, lithium fluoride, lithium chloride and lithium bromide.

8. The process according to claim 1, wherein the reaction auxiliary is lithium chloride.

9. The process according to claim 6 wherein the reaction auxiliary is lithium chloride and the basic compound is potassium hydroxide or 1,8-diazabicyclo[5,4,0]-undec-7-ene.

10. The process according to claim 1, wherein the reaction auxiliary is selected from the corresponding hydride, hydroxide, acetate, carbonate, sulphate, and halide of lithium, magnesium or aluminum.

11. The process according to claim 1, wherein the substituted triazolinone of formula II, the reaction auxiliary and the basic compound are first placed in a diluent to form a mixture and the isocynate is then slowly metered into this mixture.

* * * * *

UNITED STATES PATENT AND TRADEMARK OFFICE
CERTIFICATE OF CORRECTION

PATENT NO. : 5,708,184
DATED : January 13, 1998
INVENTOR(S) : Diehr, Hans-Joachim It is certified that error appears in the above-indentified patent and that said Letters Patent is hereby corrected as shown below:

Col. 7, line 6   Delete " of " and substitute -- or --

Signed and Sealed this

Seventeenth Day of November, 1998

Attest:

BRUCE LEHMAN

Attesting Officer    Commissioner of Patents and Trademarks